(12) United States Patent
Shimamura et al.

(10) Patent No.: US 8,497,003 B2
(45) Date of Patent: Jul. 30, 2013

(54) GLUCOSE COMPOUND, CELLULOSE COMPOSITION, CELLULOSE FILM, POLARIZING PLATE AND LIQUID CRYSTAL DISPLAY DEVICE

(75) Inventors: Satoshi Shimamura, Minami-ashigara (JP); Yoshiaki Hisakado, Minami-ashigara (JP); Naoyuki Nishikawa, Minami-ashigara (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 584 days.

(21) Appl. No.: 12/750,220

(22) Filed: Mar. 30, 2010

(65) Prior Publication Data
US 2010/0245729 A1    Sep. 30, 2010

(30) Foreign Application Priority Data
Mar. 31, 2009 (JP) .................... 2009-087821

(51) Int. Cl.
G02F 1/1335    (2006.01)
G02F 1/13363   (2006.01)
G02B 1/08      (2006.01)

(52) U.S. Cl.
USPC ....... 428/1.33; 349/96; 106/162.5; 106/162.9

(58) Field of Classification Search
USPC ............. 428/1.31, 1.33; 349/96, 122; 524/27, 524/31, 320; 536/1.11, 48, 123.1, 123.13; 106/162.5, 162, 9
See application file for complete search history.

(56) References Cited

U.S. PATENT DOCUMENTS

| | | | |
|---|---|---|---|
| 2001/0028977 A1* | 10/2001 | Kazacos et al. | 429/105 |
| 2003/0171458 A1* | 9/2003 | Buchanan et al. | 524/32 |
| 2005/0077648 A1* | 4/2005 | Sugiura | 264/216 |
| 2005/0087103 A1* | 4/2005 | Peltonen et al. | 106/206.1 |
| 2008/0122128 A1* | 5/2008 | Irie et al. | 264/1.1 |

FOREIGN PATENT DOCUMENTS
JP    2002-296421 A    10/2002

OTHER PUBLICATIONS

Chemical Listing, Benzyl 4,6-O-benzylidene-alpha-D-mannopyranoside, chemBlink, 2012.*
Hydranal, 4-Methoxyphenyl-3-o-allyl-4,6-o-benzylidene-beta-D-galactopyranoside, Santa Cruz Biotechnology Inc., Netvertise GmbH, 2012.*
JPO Website Machine English Translation of JP 2000-248258, Amanokura et al., Sep. 12, 2000.*

* cited by examiner

*Primary Examiner* — Sophie Hon
(74) *Attorney, Agent, or Firm* — Buchanan Ingersoll & Rooney PC

(57) ABSTRACT

A glucose compound represented by Formula (I):

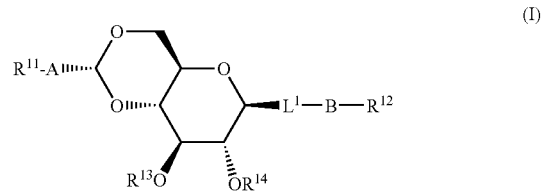

(I)

wherein, $R^{11}$ and $R^{12}$ each independently represent an alkyl group having 1 to 10 carbon atoms or an alkenyl group having 2 to 10 carbon atoms, wherein one $CH_2$ group or two or more non-adjacent $CH_2$ groups in the alkyl and alkenyl groups may be replaced by O; $L^1$ represents —OCO—*, —OCH$_2$—* (binding to B at the * side), or a single bond; A and B each independently represent a trans-1,4-cyclohexylene group which may be substituted or a 1,4-phenylene group which may be substituted; and $R^{13}$ and $R^{14}$ each independently represent a hydrogen atom or an acyl group having 1 to 10 carbon atoms; and a cellulose composition, a cellulose film, an optical film, a polarizing plate, a liquid crystal display device, and a retardation-increasing agent which have the glucose compound.

4 Claims, No Drawings

GLUCOSE COMPOUND, CELLULOSE COMPOSITION, CELLULOSE FILM, POLARIZING PLATE AND LIQUID CRYSTAL DISPLAY DEVICE

FIELD OF THE INVENTION

The present invention relates to a novel glucose compound; and a cellulose film, a polarizing plate and a liquid crystal display device, which are produced using the same and show excellent durability.

BACKGROUND OF THE INVENTION

Among cellulose films, a cellulose acetate film has higher optical isotropy (a lower retardation value) than other polymer films. Therefore, it is common to use a cellulose acetate film in applications that require optical isotropy, e.g. for a polarizing plate.

On the other hand, it is demanded that optical compensation sheets (retardation films (phase-contrast films, or phase difference films)) for use, for example, in a liquid crystal display device, have optical anisotropy (a higher retardation value). Therefore, a synthetic polymer film, e.g. a polycarbonate film or polysulfone film, which has a high retardation value, is generally used as the optical compensation sheet.

Meanwhile, in recent years, there is proposed a cellulose acetate film which has such a high retardation value that it can also be used in applications that require optical anisotropy (see, for example, JP-A-2002-296421 ("JP-A" means unexamined published Japanese patent application)). In JP-A-2002-296421, a compound described in paragraphs 0055 to 0064 is added before stretching treatment of a cellulose acetate film, for providing it with high retardation value. However, such a compound may precipitate (bleed out) on the surface of the film, depending on its compatibility with cellulose acetate, causing a concern about durability of the film.

SUMMARY OF THE INVENTION

The present invention resides in a glucose compound represented by Formula (I):

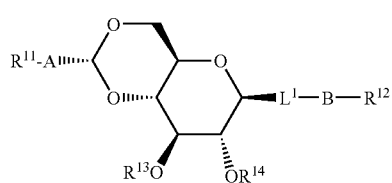

wherein, $R^{11}$ and $R^{12}$ each independently represent an alkyl group having 1 to 10 carbon atoms or an alkenyl group having 2 to 10 carbon atoms, wherein one $CH_2$ group or two or more non-adjacent $CH_2$ groups in the alkyl and alkenyl groups may be replaced by O; $L^1$ represents —COO—*, —OCH$_2$—* (binding to B at the * side), or a single bond; A and B each independently represent a trans-1,4-cyclohexylene group which may be substituted or a 1,4-phenylene group which may be substituted; and $R^{13}$ and $R^{14}$ each independently represent a hydrogen atom or an acyl group having 1 to 10 carbon atoms.

The present invention also resides in a cellulose composition, a cellulose film, an optical film, a polarizing plate, and a liquid crystal display device which comprise the aforementioned glucose compound.

Further, the present invention resides in a retardation-increasing agent, which comprises the aforementioned glucose compound.

Other and further features and advantages of the invention will appear more fully from the following description.

DETAILED DESCRIPTION OF THE INVENTION

According to the present invention, there is provided the following means:

(1) A glucose compound represented by Formula (I):

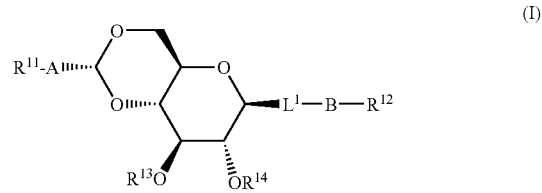

wherein, $R^{11}$ and $R^{12}$ each independently represent an alkyl group having 1 to 10 carbon atoms or an alkenyl group having 2 to 10 carbon atoms, wherein one $CH_2$ group or two or more non-adjacent $CH_2$ groups in the alkyl and alkenyl groups may be replaced by O; $L^1$ represents —OCO—*, —OCH$_2$—* (binding to B at the * side), or a single bond; A and B each independently represent a trans-1,4-cyclohexylene group which may be substituted or a 1,4-phenylene group which may be substituted; and $R^{13}$ and $R^{14}$ each independently represent a hydrogen atom or an acyl group having 1 to 10 carbon atoms.

(2) The glucose compound described in the above item (1), wherein the compound represented by Formula (I) is a compound represented by Formula (II):

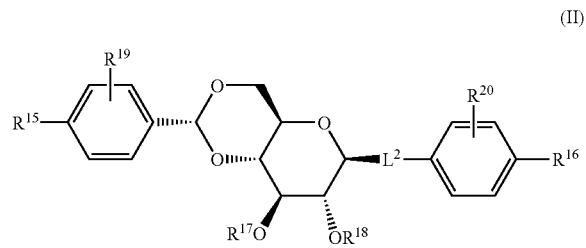

wherein, $R^{15}$ and $R^{16}$ each independently represent an alkyl group having 1 to 6 carbon atoms or an alkenyl group having 2 to 5 carbon atoms, wherein one $CH_2$ group or two or more non-adjacent $CH_2$ groups in the alkyl and alkenyl groups may be replaced by O; $L^2$ represents —OCO—* or —OCH$_2$—* (binding to the phenylene group at the * side); $R^{17}$ and $R^{18}$ each independently represent a hydrogen atom or an acyl group having 1 to 10 carbon atoms; and $R^{19}$ and $R^{20}$ each independently represent a hydrogen atom, a methyl group or a methoxy group.

(3) A cellulose composition, comprising at least one kind of a cellulose compound and at least one kind of glucose compound described in the above item (1) or (2).

(4) A cellulose film, comprising the cellulose composition described in the above item (3).

(5) An optical film, comprising the cellulose film described in the above item (4).

(6) A polarizing plate, comprising a polarization film and two transparent protective films placed on both sides of the polarization film, wherein at least one of the transparent protective films is the optical film described in the above item (5).
(7) A liquid crystal display device, comprising a liquid crystal cell and two polarizing plates placed on both sides of the liquid crystal cell, wherein at least one of the polarizing plates is the polarizing plate described in the above item (6).
(8) The liquid crystal display device described in the above item (7), wherein a display mode of the liquid crystal display device is a VA mode.
(9) A retardation-increasing agent comprising the glucose compound described in the above item (1) or (2).

Hereinafter, the present invention will be described in detail. The descriptions below may be given based on some representative embodiments or examples of elements of the present invention, but the invention is not meant to be limited to such embodiments or examples. In the present specification, "to" denotes a range including numerical values described before and after it as a minimum value and a maximum value.

[Glucose Compound]

First, the glucose compound represented by Formula (I) will be described in detail.

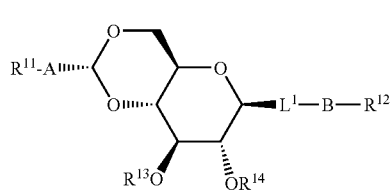

In Formula (I), $R^{11}$ and $R^{12}$ each independently represent an alkyl group having 1 to 10 carbon atoms or an alkenyl group having 2 to 10 carbon atoms, wherein one $CH_2$ group or two or more non-adjacent $CH_2$ groups in the alkyl and alkenyl groups may be replaced by O; $L^1$ represents —OCO—*, —OCH$_2$—* (binding to B at the * side), or a single bond; A and B each independently represent a trans-1,4-cyclohexylene group which may be substituted or a 1,4-phenylene group which may be substituted; and $R^{13}$ and $R^{14}$ each independently represent a hydrogen atom or an acyl group having 1 to 10 carbon atoms.

Each of $R^{11}$ and $R^{12}$ is preferably an alkyl group having 1 to 10 carbon atoms, an alkoxy group having 1 to 10 carbon atoms, an alkoxyalkyl group having 1 to 10 carbon atoms or an alkenyl group having 2 to 10 carbon atoms; more preferably an alkyl group having 1 to 6 carbon atoms, an alkoxy group having 1 to 6 carbon atoms, an alkoxyalkyl group having 1 to 6 carbon atoms or an alkenyl group having 2 to 5 carbon atoms; still more preferably an ethyl group, a n-propyl group, a n-butyl group, a n-pentyl group, a methoxy group, an ethoxy group, a n-propoxy group, a n-butoxy group or an allyl group; and most preferably a methoxy group. $R^{11}$ and $R^{12}$ may be the same as or different from each other.

$L^1$ represents —COO—*, —OCH$_2$—* (binding to B at the * side) or a single bond, preferably —OCO—* or —OCH$_2$—*.

A and B each independently represent a trans-1,4-cyclohexylene group or a 1,4-phenylene group; preferably a 1,4-phenylene group. The rings A and B may be substituted, and examples of favorable substituent groups include a methyl group, an ethyl group, a methoxy group and the like, but the rings are more preferably unsubstituted or substituted with one or more methyl groups.

$R^{13}$ and $R^{14}$ each independently represent a hydrogen atom or an acyl group having 1 to 10 carbon atoms; preferably a hydrogen atom, an acetyl group, a propionyl group, a butylyl group or a benzoyl group; more preferably a hydrogen atom or an acetyl group. $R^{13}$ and $R^{14}$ may be the same as or different from each other.

Among the compounds represented by Formula (I), glucose compounds represented by the following Formula (II) are preferable.

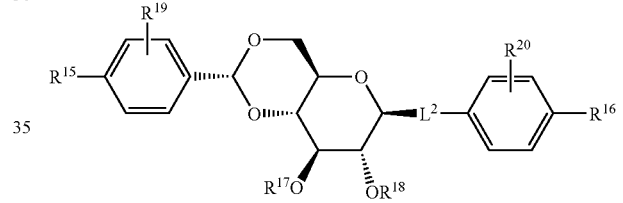

In Formula (II), $R^{15}$ and $R^{16}$ each independently represent an alkyl group having 1 to 6 carbon atoms or an alkenyl group having 2 to 5 carbon atoms, wherein one $CH_2$ group or two or more non-adjacent $CH_2$ groups in the alkyl and alkenyl groups may be replaced by O; $L^2$ represents —OCO—* or —OCH$_2$—* (binding to the phenylene group at the * side); $R^{17}$ and $R^{18}$ each independently represent a hydrogen atom or an acyl group having 1 to 10 carbon atoms; and $R^{19}$ and $R^{29}$ each independently represent a hydrogen atom, a methyl group or a methoxy group.

Specific examples of the compound represented by Formula (I) or Formula (II) will be given below, though the present invention is not limited to these specific examples. In the present specification, Ac represents an acetyl group.

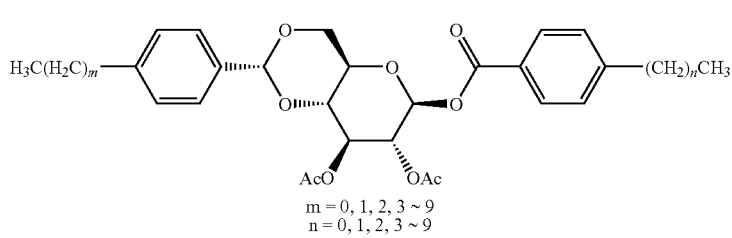

(A-1)

m = 0, 1, 2, 3 ~ 9
n = 0, 1, 2, 3 ~ 9

-continued
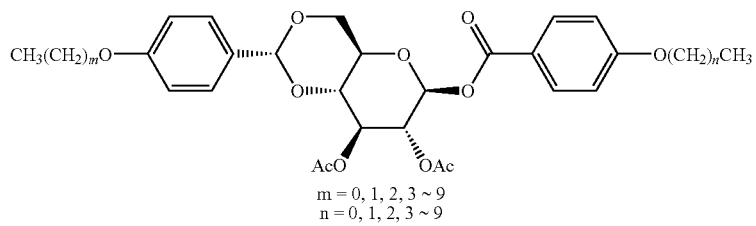
(A-2)
m = 0, 1, 2, 3 ~ 9
n = 0, 1, 2, 3 ~ 9
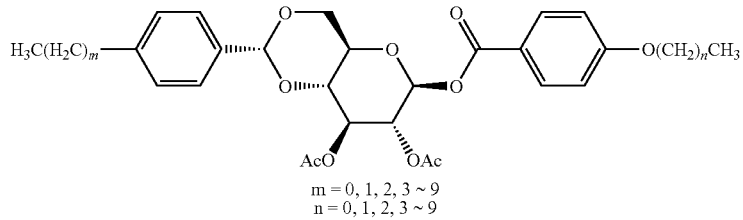
(A-3)
m = 0, 1, 2, 3 ~ 9
n = 0, 1, 2, 3 ~ 9
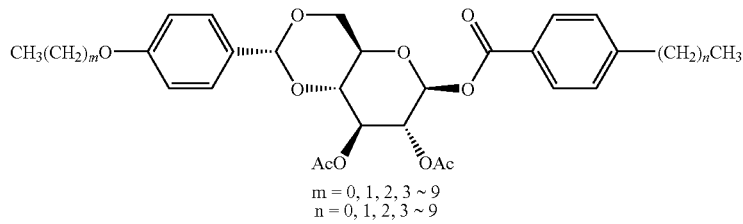
(A-4)
m = 0, 1, 2, 3 ~ 9
n = 0, 1, 2, 3 ~ 9
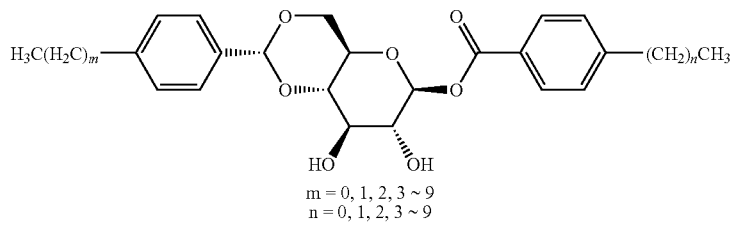
(A-5)
m = 0, 1, 2, 3 ~ 9
n = 0, 1, 2, 3 ~ 9
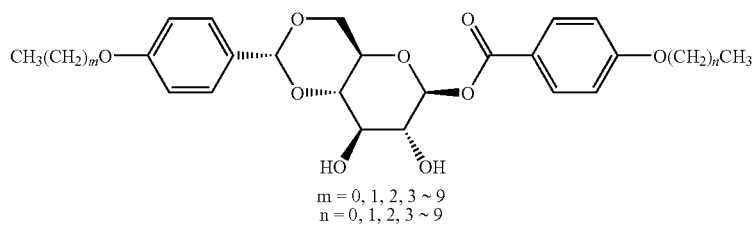
(A-6)
m = 0, 1, 2, 3 ~ 9
n = 0, 1, 2, 3 ~ 9
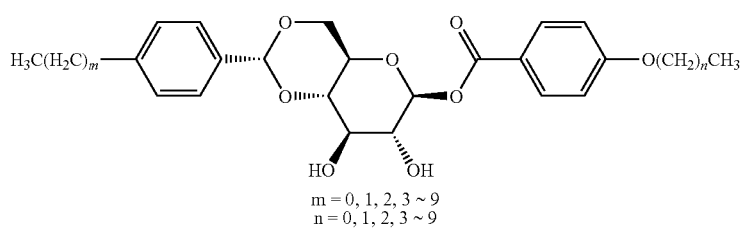
(A-7)
m = 0, 1, 2, 3 ~ 9
n = 0, 1, 2, 3 ~ 9
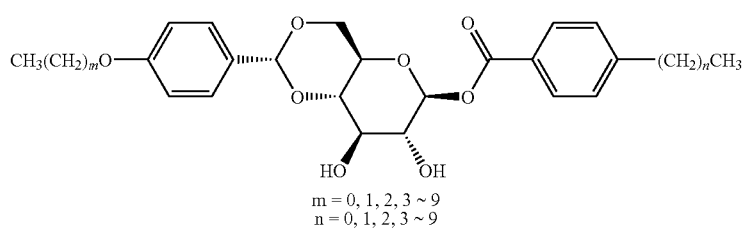
(A-8)
m = 0, 1, 2, 3 ~ 9
n = 0, 1, 2, 3 ~ 9

-continued
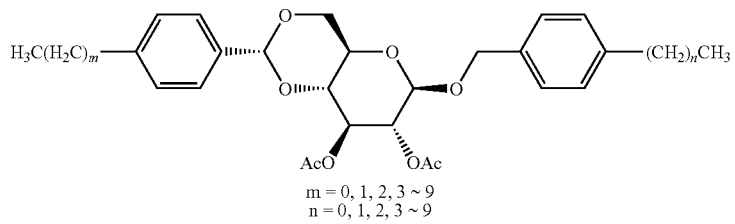
(B-1)
m = 0, 1, 2, 3 ~ 9
n = 0, 1, 2, 3 ~ 9
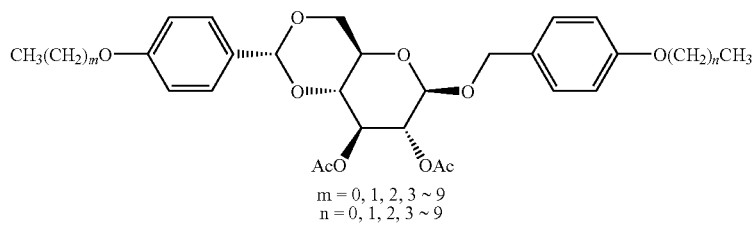
(B-2)
m = 0, 1, 2, 3 ~ 9
n = 0, 1, 2, 3 ~ 9
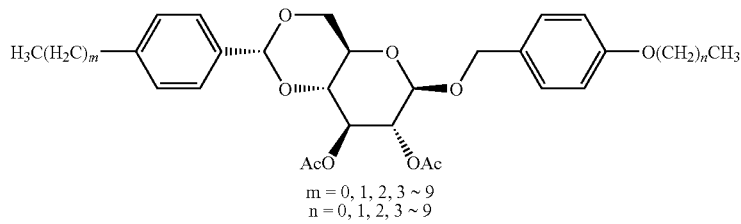
(B-3)
m = 0, 1, 2, 3 ~ 9
n = 0, 1, 2, 3 ~ 9
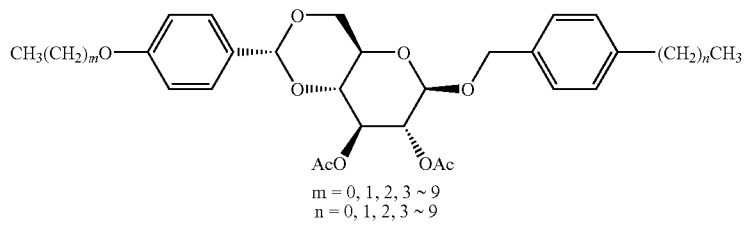
(B-4)
m = 0, 1, 2, 3 ~ 9
n = 0, 1, 2, 3 ~ 9
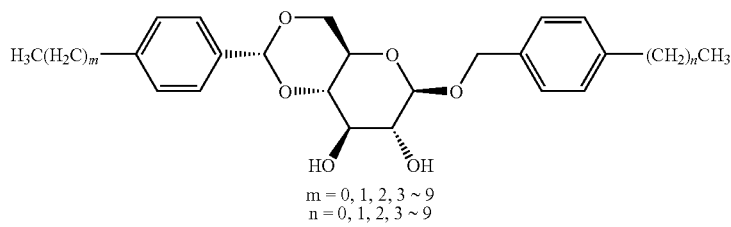
(B-5)
m = 0, 1, 2, 3 ~ 9
n = 0, 1, 2, 3 ~ 9
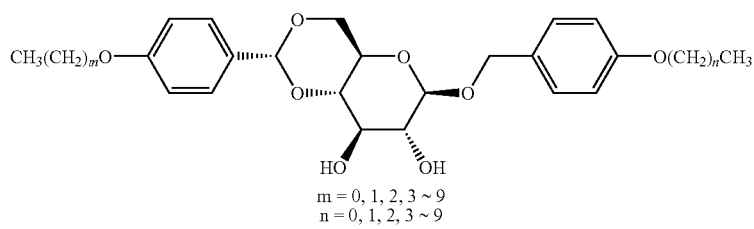
(B-6)
m = 0, 1, 2, 3 ~ 9
n = 0, 1, 2, 3 ~ 9
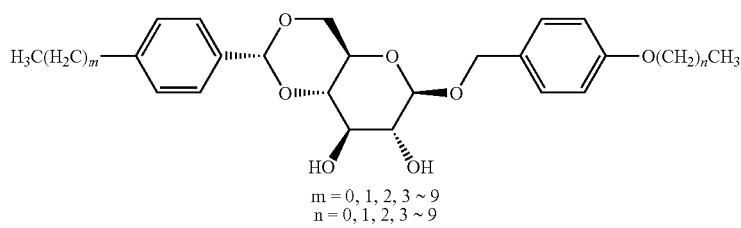
(B-7)
m = 0, 1, 2, 3 ~ 9
n = 0, 1, 2, 3 ~ 9

-continued
(B-8)
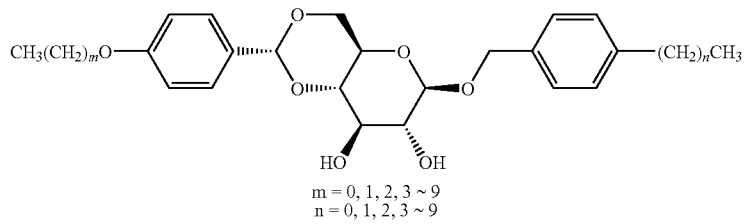
m = 0, 1, 2, 3 ~ 9
n = 0, 1, 2, 3 ~ 9
(C-1)
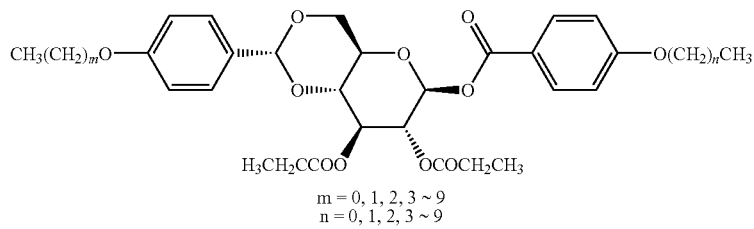
m = 0, 1, 2, 3 ~ 9
n = 0, 1, 2, 3 ~ 9
(C-2)
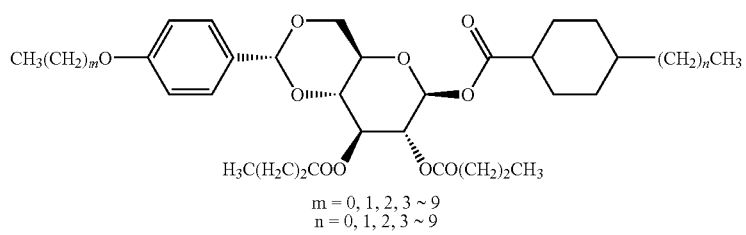
m = 0, 1, 2, 3 ~ 9
n = 0, 1, 2, 3 ~ 9
(C-3)
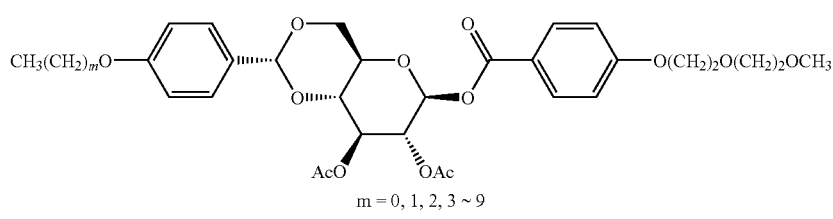
m = 0, 1, 2, 3 ~ 9
(C-4)
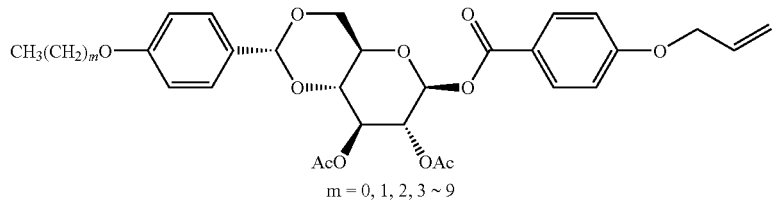
m = 0, 1, 2, 3 ~ 9
(C-5)
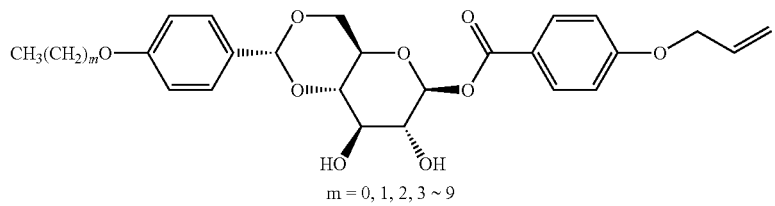
m = 0, 1, 2, 3 ~ 9
(C-6)
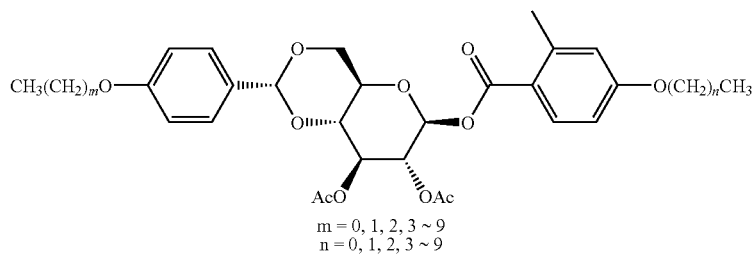
m = 0, 1, 2, 3 ~ 9
n = 0, 1, 2, 3 ~ 9

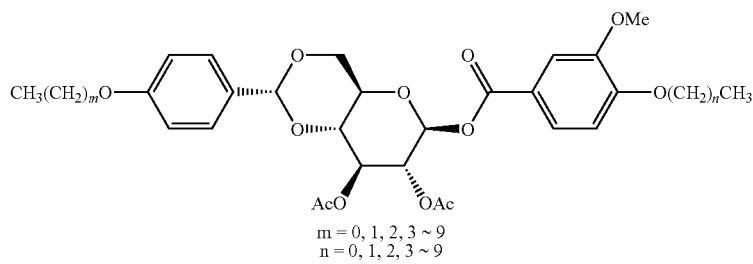

(C-7)

m = 0, 1, 2, 3 ~ 9
n = 0, 1, 2, 3 ~ 9

The compound represented by Formula (I) of the present invention can be synthesized from (D)-glucose according to the scheme shown below. For example, J. Am. Chem. Soc., 2000, 124 (33), pp. 9756-9767 describes a method of synthesizing an intermediate B by acetal exchange of (D)-glucose, acylation and subsequent selective deacylation on the 1-positioned hydroxyl group. As a method subsequently used for conversion of the intermediate B to a glucose compound A, any esterification reaction, for example a method using a corresponding acid halide or a condensing agent, may be employed. A glucose compound B can be obtained, for example by a method of converting it to an intermediate C and then glycosylating it with a corresponding alcohol, according to the method described in Carbohyd. Res. 1985, 135, 203., or Angew. Chem., Int. Ed. Engl. 1986, 25, 212. However, the synthesis method for the compound of the present invention is not limited to the methods described above.

The compound represented by Formula (I) or (II) can be used as a retardation-increasing agent (adjusting agent) for an optical film, and favorably as a retardation-increasing agent used in preparation of a film that particularly shows excellent Re expression by stretching. The compound represented by Formula (I) or (II) is useful particularly as a retardation-increasing agent for cellulose films. A method of producing a film containing these compounds, for example, will be described below in detail.

[Cellulose Composition]

The cellulose composition of the present invention is a composition comprising the cellulose compound and the compound represented by Formula (I) or (II). In the present invention, the term "cellulose compound" refers to a compound having cellulose as a basic structure. In the present invention, the cellulose compound also means a compound having a cellulose skeleton obtained by introducing a functional group biologically or chemically into a cellulose to be

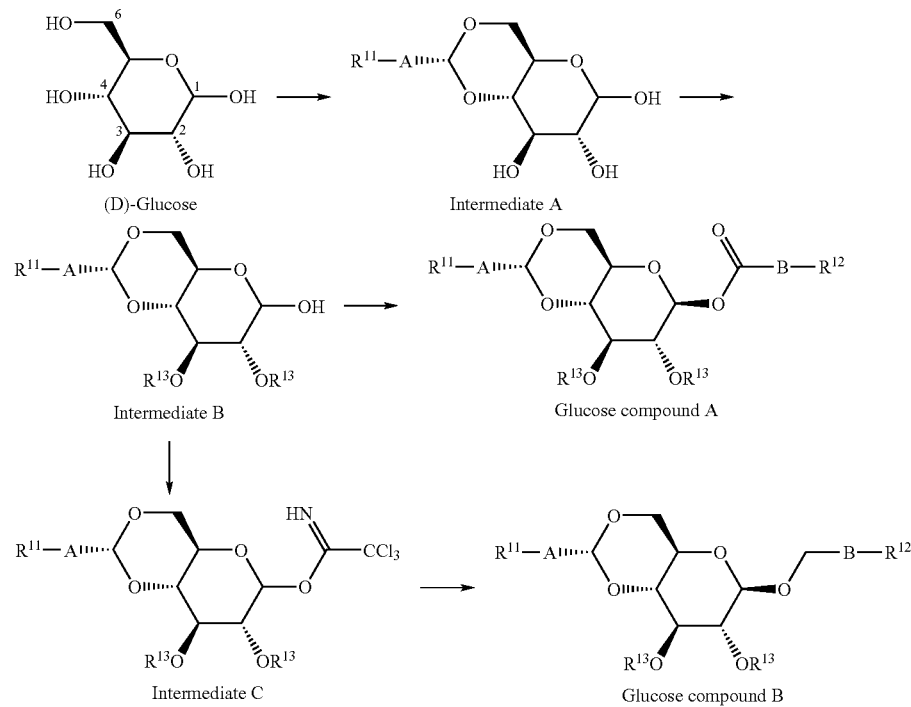

The content of the compound represented by Formula (I) or (II) in the cellulose composition of the present invention is preferably 0.1 to 15 mass %, more preferably 0.5 to 10 mass %, and still more preferably 1 to 5 mass %, with respect to the cellulose compound.

used as a raw material. The cellulose compound is preferably a cellulose ester, and more preferably a cellulose acylate (examples thereof include a cellulose triacylate and a cellulose acylate propionate). Further, in the present invention, two or more cellulose compounds different from each other may be blended to use.

A preferred embodiment of the cellulose compound that can be used in the present invention will be explained below, in which a cellulose acylate is to be an exemplified example.

The cellulose acylates preferable among cellulose compounds include the following materials. That is, with respect to the degree of substitution for hydroxyl groups of cellulose, cellulose acylates satisfying all of the relations (a) to (c) defined below are used to advantage:

$$1.0 \leq SA+SB \leq 3.0 \quad \text{(a)}$$

$$0.5 \leq SA \leq 3.0 \quad \text{(b)}$$

$$0 \leq SB \leq 1.5 \quad \text{(c)}$$

In these relations, SA and SB represent degrees of substitution of acyl groups for hydroxyl groups of cellulose, and more specifically SA is the degree of acetyl substitution and SB is the degree of acyl substitution having 3 to 22 carbon atoms. The glucose units having a β-1, 4 bond and forming the cellulose have free hydroxyl groups in the 2-, 3- and 6-positions thereof. The cellulose acylate is a polymer obtained by esterifying a part or all of those hydroxyl groups. Its acyl substitution degree means the total of the esterification degrees of cellulose in the 2-, 3- and 6-positions (an esterification degree of 100% meaning a substitution degree of 1). In the present invention, the total of the SA and SB in the hydroxyl groups is more preferably from 1.50 to 2.96, even more preferably from 2.00 to 2.95. The SB is preferably from 0 to 1.5, more preferably from 0 to 1.0. Also preferably, at least 28% of SB is for the substituent of the 6-positioned hydroxyl group, more preferably at least 30% of SB is for the substituent of the 6-positioned hydroxyl group, even more preferably at least 35% of SB is for the substituent of the 6-positioned hydroxyl group, and particularly preferably at least 40% of SB is for the substituent of the 6-positioned hydroxyl group. The total of the SA and the SB in the hydroxyl groups at the 6 positions in the cellulose acylate is preferably 0.8 or more, more preferably 0.85 or more, even more preferably 0.90 or more.

The cellulose acylate for use in the present invention, the acyl substituent having 3 to 22 carbon atoms as SB may be aliphatic acyl groups or aromatic acyl groups, and is not particularly limited. The acyl substituent may be an alkylcarbonyl ester of cellulose, an alkenylcarbonyl ester of cellulose, an aromatic carbonyl ester of cellulose or an aromatic alkylcarbonyl ester of cellulose. These esters may have a substituent. Preferable examples of the substituents include a propionyl group, a butanoyl group, a heptanoyl group, a hexanoyl group, an octanoyl group, a decanoyl group, a dodecanoyl group, a tridecanoyl group, a tetradecanoyl group, a hexadecanoyl group, an octadecanoyl group, an isobutanoyl group, a pivaloyl group, a cyclohexanecarbonyl group, an oleoyl group, a benzoyl group, a naphthylcarbonyl group and a cinnamoyl group. A propionyl group, a butanoyl group, a dodecanoyl group, an octadecanoyl group, a pivaloyl group, an oleoyl group, a benzoyl group, a naphthylcarbonyl group and a cinnamoyl group are more preferred.

The basic principle of the synthesis method of cellulose acylate is described in Migita, et al., Mokuzai Kagaku (Wood Chemistry), pp. 180-190, Kyoritsu Shuppan (1968). A representative synthesis method is a liquid phase acetylation method using a carboxylic anhydride-an acetic acid-a sulfuric acid catalyst. More specifically, a cellulose raw material such as cotton linter and wood pulp is pretreated with an appropriate amount of acetic acid and then charged into a previously cooled carboxylating mixed solution to esterify the cellulose, thereby synthesizing a complete cellulose acylate (the total of acyl substitution degrees at the 2-position, 3-position and 6-position is almost 3.00). The carboxylating mixed solution generally contains an acetic acid as a solvent, a carboxylic anhydride as an esterifying agent, and a sulfuric acid as a catalyst.

The carboxylic anhydride is usually used stoichiometrically in excess of the total of the cellulose with which the carboxylic acid reacts, and the moisture present in the system. After the completion of acylation reaction, an aqueous solution of neutralizer (for example, carbonate, acetate or oxide of calcium, magnesium, iron, aluminum or zinc) is added for hydrolyzing the excess carboxylic anhydride remaining in the system and partially neutralizing the esterification catalyst. The obtained complete cellulose acylate is kept at 50 to 90° C. in the presence of a slight amount of an acetylation reaction catalyst (generally, the remaining sulfuric acid), whereby the cellulose acylate is saponified and ripened and is changed to a cellulose acylate having desired acyl substitution degree and polymerization degree. At the time when the desired cellulose acylate is obtained, the cellulose acylate solution is charged into water or dilute sulfuric acid (alternatively, water or dilute sulfuric acid is charged into the cellulose acylate solution) with or without neutralizing the catalyst remaining in the system by using a neutralizing agent described above, thereby separating the cellulose acylate, and after washing and stabilization treatment, the cellulose acylate is obtained.

The polymerization degree of the cellulose acylate preferably used in the present invention is, in terms of viscosity average polymerization degree, preferably from 200 to 700, more preferably 250 to 550, still more preferably from 250 to 400, yet still more preferably from 250 to 350. The average molecular weight can be measured by the limiting viscosity method of Uda, et al. (Kazuo Uda and Hideo Saito, JOURNAL OF THE SOCIETY OF FIBER SCIENCE AND TECHNOLOGY, JAPAN, Vol. 18, No. 1, pp. 105-120 (1962)). Furthermore, this is described in detail in JP-A-9-95538.

When low molecular components are removed, the average molecular weight (polymerization degree) increases, but the viscosity becomes lower than that of normal cellulose acylate and this is useful. The cellulose acylate reduced in low molecular components can be obtained by removing low molecular components from a cellulose acylate synthesized by a normal method. The low molecular components can be removed by washing the cellulose acylate with an appropriate organic solvent.

In the case of producing a cellulose acylate reduced in low molecular components, the amount of the sulfuric acid catalyst in the acetylation reaction is preferably adjusted to be from 0.5 to 25 parts by mass per 100 parts by mass of cellulose. When the amount of the sulfuric acid catalyst is adjusted to this range, a cellulose acylate preferred also in view of the molecular weight distribution (having a uniform molecular weight distribution) can be synthesized. In use for the production of the cellulose acylate film of the present invention, the water content of the cellulose acylate is preferably 2 mass % or less, more preferably 1 mass % or less. In particular, a cellulose acylate having a water content of 0.7 mass % or less is preferred. The cellulose acylate in general contains water and the water content is known to be from 2.5 to 5 mass %. For obtaining this water content of cellulose acylate in the present invention, the cellulose acylate needs to be dried, and the method therefor is not particularly limited as long as the objective water content (for example, 2 mass % or less) can be obtained.

The raw material cotton and synthesis method of the cellulose acylate for use in the present invention are described in detail in JIII Journal of Technical Disclosure (No. 2001-1745, pp. 7-12, Japan Institute of Invention and Innovation (Mar. 15, 2001)).

The content of the cellulose compound in the cellulose composition of the present invention is preferably 55 mass % or more, more preferably 70 mass % or more, and still more preferably 80 mass % or more, with respect to the total amount of the solid matters. In preparation of the cellulose composition of the present invention, particles of a cellulose acylate is preferably used as a raw material for film production. It is preferable that 90% or more by mass of the particles has a particle diameter of 0.5 to 5 mm, and 50% or more by mass of the particles has a particle diameter of 1 to 4 mm. The shapes of the cellulose acylate particles are preferably made as completely spherical as possible.

The cellulose composition of the present invention may contain, in addition to the cellulose compound and the compound represented by Formula (I), various additives in each preparation step according to application (such as plasticizers, ultraviolet inhibitors, antidegradants, optical anisotropy-controlling agents, fine particles, releasing agents, infrared absorbents and others). The additive(s) may be in a solid or oily state. That is, there is no particular limitation to the melting points or boiling points of the additives. For example, an ultraviolet absorber having a melting point of less than 20° C. and an ultraviolet absorber having a melting point of 20° C. or more may be used in combination; or, similarly, plasticizers may be used in combination. Specifically, the method described in JP-A-2001-151901 can be applied to the present invention. Examples of the infrared absorber include those described in JP-A-2001-194522. These additives may be added at any stage in the dope preparation process, but a step of adding the additives to prepare a dope may be added as a final preparation step of the dope preparation process.

The amount of each material added is not particularly limited as long as its function can be exerted. When the cellulose film composed of the cellulose composition is a multilayer film, the kind or amount added of the additive may be different among respective layers. This is a conventionally known technique described, for example, in JP-A-2001-151902.

Furthermore, additives described in detail in JIII Journal of Technical Disclosure (No. 2001-1745, pages 16 to 22 et seq., Japan Institute of Invention and Innovation (Mar. 15, 2001)) can be appropriately used.

The organic solvent used to dissolve the cellulose compound, preferably the cellulose acylate, in the present invention will be described hereinafter.

The chlorine-free organic solvent preferably used at the preparation of a solution of cellulose compound preferably used in the present invention is described below. In the present invention, the chlorine-free organic solvent is not particularly limited as long as its purpose can be achieved and the cellulose compound can be dissolved, cast and film-formed. The chlorine-free organic solvent for use in the present invention is preferably a solvent selected from an ester, a ketone and an ether each having 3 to 12 carbon atoms.

The ester, ketone and ether each have a ring structure. A compound having two or more functional groups of an ester, a ketone and an ether (that is, —O—, —CO— and —COO—) may also be used as the main solvent, and the compound may have another functional group such as alcoholic hydroxyl group. In the case of a main solvent having two or more kinds of functional groups, the number of carbon atoms may suffice if it falls within the range specified for the compound having any one of the functional groups.

Examples of the esters having a carbon number of 3 to 12 include ethyl formate, propyl formate, pentyl formate, methyl acetate, ethyl acetate and pentyl acetate. Examples of the ketones having a carbon number of 3 to 12 include acetone, methyl ethyl ketone, diethyl ketone, diisobutyl ketone, cyclopentanone, cyclohexanone, and methylcyclohexanone. Examples of the ethers having a carbon number of 3 to 12 include diisopropyl ether, dimethoxymethane, dimethoxyethane, 1,4-dioxane, 1,3-dioxolane, tetrahydrofuran, anisole and phenetole. Examples of the organic solvent having two or more kinds of functional groups include 2-ethoxyethyl acetate, 2-methoxyethanol and 2-butoxyethanol.

The chlorine-free organic solvent preferably used for the solution of cellulose compound is selected from various aspects described above, but is preferably as follows. The chlorine-free solvent is preferably a mixed solvent comprising three or more different kinds of solvents and in which the first solvent is at least one member selected from methyl acetate, ethyl acetate, methyl formate, ethyl formate, acetone, dioxolane and dioxane, or a mixed solution thereof, the second solvent is selected from ketones having a carbon number of 4 to 7 and acetoacetic acid esters, and the third solvent is selected from alcohols having a carbon number of 1 to 10 and hydrocarbons, preferably from alcohols having a carbon number of 1 to 8.

When the first solvent is a mixed solution of two or more kinds of solvents, the second solvent may be omitted. The first solvent is preferably methyl acetate, acetone, methyl formate, ethyl formate or a mixture thereof, and the second solvent is preferably methyl ethyl ketone, cyclopentanone, cyclohexanone or methyl acetylacetate and may be a mixed solvent thereof.

In the alcohol as the third solvent, the hydrocarbon chain may be linear, branched or cyclic, and a saturated aliphatic hydrocarbon chain is preferred. The hydroxyl group of the alcohol may be primary, secondary or tertiary. Examples of the alcohol include methanol, ethanol, 1-propanol, 2-propanol, 1-butanol, 2-butanol, tert-butanol, 1-pentanol, 2-methyl-2-butanol and cyclohexanol. Also, a fluorine-based alcohol may be used as the alcohol. Examples thereof include 2-fluoroethanol, 2,2,2-trifluoroethanol and 2,2,3,3-tetrafluoro-1-propanol.

The hydrocarbon may be linear, branched or cyclic, and either an aromatic hydrocarbon or an aliphatic hydrocarbon can be used. The aliphatic hydrocarbon may be either saturated or unsaturated. Examples of the hydrocarbon include cyclohexane, hexane, benzene, toluene and xylene. These alcohols and hydrocarbons as the third solvent may be used individually or as a mixture of two or more kinds thereof and this is not particularly limited. Specific preferred compounds of the alcohol as the third solvent include methanol, ethanol, 1-propanol, 2-propanol, 1-butanol, 2-butanol and cyclohexanol, and specific preferred examples of the hydrocarbon include cyclohexane and hexane. Among these, more preferred are methanol, ethanol, 1-propanol, 2-propanol and 1-butanol.

The mixing ratio of these three kinds of solvents is, based on the entire amount of the mixed solvent, preferably such that the first solvent is from 20 to 95 mass %, the second solvent is from 2 to 60 mass % and the third solvent is from 2 to 30 mass %, more preferably such that the first solvent is from 30 to 90 mass %, the second solvent is from 3 to 50 mass % and the alcohol as the third solvent is from 3 to 25 mass %, still more preferably such that the first solvent is from 30 to 90 mass %, the second solvent is from 3 to 30 mass % and the third solvent is an alcohol and occupies from 3 to 15 mass %.

When the first solvent is a mixed liquid and the second solvent is not used at all, the first solvent and the third solvent are contained preferably at proportions of 20 to 90% by mass and 10 to 80% by mass, respectively, more preferably at proportions of 30 to 86% by mass and 14 to 70% by mass, respectively. The chlorine-free organic solvent for use in the present invention is described in more detail in JIII Journal of Technical Disclosure (No. 2001-1745, pp. 12-16, Japan Institute of Invention and Innovation (Mar. 15, 2001)). Preferred examples of the combination of chlorine-free organic solvents for use in the present invention include, but are not limited to, the following compositions.

methyl acetate/acetone/methanol/ethanol/butanol (75/10/5/5/5, parts by mass),
methyl acetate/acetone/methanol/ethanol/propanol (75/10/5/5/5, parts by mass),
methyl acetate/acetone/methanol/butanol/cyclohexane (75/10/5/5/5, parts by mass),
methyl acetate/acetone/ethanol/butanol (81/8/7/4, parts by mass),
methyl acetate/acetone/ethanol/butanol (82/10/4/4, parts by mass),
methyl acetate/acetone/ethanol/butanol (80/10/4/6, parts by mass),
methyl acetate/methyl ethyl ketone/methanol/butanol (80/10/5/5, parts by mass),
methyl acetate/acetone/methyl ethyl ketone/ethanol/isopropanol (75/10/10/5/7, parts by mass),
methyl acetate/cyclopentanone/methanol/isopropanol (80/10/5/8, parts by mass),
methyl acetate/acetone/butanol (85/5/5, parts by mass),
methyl acetate/cyclopentanone/acetone/methanol/butanol (60/15/15/5/6, parts by mass),
methyl acetate/cyclohexanone/methanol/hexane (70/20/5/5, parts by mass),
methyl acetate/methyl ethyl ketone/acetone/methanol/ethanol (50/20/20/5/5, parts by mass),
methyl acetate/1,3-dioxolane/methanol/ethanol (70/20/5/5, parts by mass),
methyl acetate/dioxolane/acetone/methanol/ethanol (60/20/10/5/5, parts by mass),
methyl acetate/acetone/cyclopentanone/ethanol/isobutanol/cyclohexane (65/10/10/5/5/5, parts by mass),
methyl formate/methyl ethyl ketone/acetone/methanol/ethanol (50/20/20/5/5, parts by mass),
methyl formate/acetone/ethyl acetate/ethanol/butanol/hexane (65/10/10/5/5/5, parts by mass),
acetone/methyl acetoacetate/methanol/ethanol (65/20/10/5, parts by mass),
acetone/cyclopentanone/ethanol/butanol (65/20/10/5, parts by mass),
acetone/1,3-dioxolane/ethanol/butanol (65/20/10/5, parts by mass), and 1,3-dioxolane/cyclohexanone/methyl ethyl ketone/methanol/butanol (55/20/10/5/5/5, parts by mass).

In addition to the above-described chlorine-free organic solvent, the solution of cellulose compound for use in the present invention may contain dichloromethane in an amount of 10 mass % or less based on the entire amount of organic solvents used in the present invention.

At the preparation of a solution of cellulose compound (composition) in the present invention, a chlorine-based organic solvent may be used as the main solvent. In the present invention, the kind of the chlorine-based organic solvent is not particularly limited as long as its purpose can be achieved and the cellulose compound can be dissolved, cast and film-formed. The chlorine-based organic solvent is preferably dichloromethane or chloroform, more preferably dichloromethane.

An organic solvent other than the chlorine-based organic solvent may also be mixed without any particular problem. In this case, dichloromethane is preferably used to occupy at least 50 mass % in the entire amount of organic solvents. The other organic solvent used in combination with the chlorine-based organic solvent as the main solvent is described below. The other organic solvent is preferably a solvent selected from an ester, a ketone, an ether, an alcohol, a hydrocarbon and the like each having a carbon number of 3 to 12. The ester, ketone, ether and alcohol each may have a cyclic structure. A compound having two or more functional groups of an ester, a ketone and an ether (that is, —O—, —CO— and —COO—) may also be used as the solvent, and the compound may have another functional group such as alcoholic hydroxyl group at the same time. In the case of a solvent having two or more kinds of functional groups, the number of carbon atoms may suffice if it falls within the range specified for the compound having any one functional group. Examples of the esters having a carbon number of 3 to 12 include ethyl formate, propyl formate, pentyl formate, methyl acetate, ethyl acetate and pentyl acetate.

Examples of the ketones having a carbon number of 3 to 12 include acetone, methyl ethyl ketone, diethyl ketone, diisobutyl ketone, cyclopentanone, cyclohexanone and methylcyclohexanone. Examples of the ethers having a carbon number of 3 to 12 include diisopropyl ether, dimethoxymethane, dimethoxyethane, 1,4-dioxane, 1,3-dioxolane, tetrahydrofuran, anisole and phenetole. Examples of the organic solvent having two or more kinds of functional groups include 2-ethoxyethyl acetate, 2-methoxyethanol and 2-butoxyethanol.

The alcohol used in combination with the chlorine-based organic solvent may be linear, branched or cyclic. In particular, a saturated aliphatic hydrocarbon is preferred. The hydroxyl group of the alcohol may be primary, secondary or tertiary. Examples of the alcohol include methanol, ethanol, 1-propanol, 2-propanol, 1-butanol, 2-butanol, tert-butanol, 1-pentanol, 2-methyl-2-butanol and cyclohexanol. Also, a fluorine-based alcohol may be used as the alcohol. Examples thereof include 2-fluoroethanol, 2,2,2-trifluoroethanol and 2,2,3,3-tetrafluoro-1-propanol.

The hydrocarbon may be linear, branched or cyclic, and either an aromatic hydrocarbon or an aliphatic hydrocarbon can be used. The aliphatic hydrocarbon may be saturated or unsaturated. Examples of the hydrocarbon include cyclohexane, hexane, benzene, toluene and xylene.

The chlorine-free organic solvent which is used in combination with the chlorine-based organic solvent which is a main solvent used for the cellulose compound is not particularly limited. The chlorine-free organic solvent is selected from methyl acetate, ethyl acetate, methyl formate, ethyl formate, acetone, dioxolane, dioxane, ketones and acetoacetic acid esters each having 4 to 7 carbon atoms, and alcohols and hydrocarbons each having 1 to 10 carbon atoms. Preferable examples of the chlorine-free organic solvent used in combination with include methyl acetate, acetone, methyl formate, ethyl formate, methyl ethyl ketone, cyclopentanone, cyclohexanone, methyl acetylacetate, methanol, ethanol, 1-propanol, 2-propanol, 1-butanol, 2-butanol, cyclohexanol, cyclohexane, and hexane. Preferable examples of the combination of the chlorine-based organic solvents as a main solvent and the chlorine-free organic solvents are described below. However, the combination is not limited to these examples.

dichloromethane/methanol/ethanol/butanol (75/10/5/5, parts by mass),
dichloromethane/acetone/methanol/propanol (80/10/5/5, parts by mass)
dichloromethane/methanol/butanol/cyclohexane (75/10/5/5, parts by mass),
dichloromethane/methyl ethyl ketone/methanol/butanol (80/10/5/5, parts by mass),
dichloromethane/acetone/methyl ethyl ketone/ethanol/isopropanol (75/10/10/5/7, parts by mass),
dichloromethane/cyclopentanone/methanol/isopropanol (80/10/5/8, parts by mass),
dichloromethane/methyl acetate/butanol (80/10/10, parts by mass),
dichloromethane/cyclohexanone/methanol/hexane (70/20/5/5, parts by mass),
dichloromethane/methyl ethyl ketone/acetone/methanol/ethanol (50/20/20/5/5, parts by mass),
dichloromethane/1,3-dioxolane/methanol/ethanol (70/20/5/5, parts by mass),
dichloromethane/dioxane/acetone/methanol/ethanol (60/20/10/5/5, parts by mass),
dichloromethane/acetone/cyclopentanone/ethanol/isobutanol/cyclohexane (65/10/10/5/5/5, parts by mass),
dichloromethane/methyl ethyl ketone/acetone/methanol/ethanol (70/10/10/5/5, parts by mass),
dichloromethane/acetone/ethyl acetate/ethanol/butanol/hexane (65/10/10/5/5/5, parts by mass),
dichloromethane/methyl acetoacetate/methanol/ethanol (65/20/10/5, parts by mass), and
dichloromethane/cyclopentanone/ethanol/butanol (65/20/10/5, parts by mass).

In the present invention, it is preferable that a diluted cellulose compound solution obtained by diluting a dope containing the cellulose compound, preferably the cellulose acylate, with the above described organic solvent to give a concentration of from 0.1 to 5% by mass has an aggregate molecular weight of cellulose compound (preferably the cellulose acylate) of from 150,000 to 15,000,000, more preferably from 180,000 to 9,000,000. The aggregate molecular weight can be determined by a static light scattering method. The cellulose compound (preferably the cellulose acylate) is preferably dissolved such that the squared radius of inertia simultaneously determined by this method becomes from 10 to 200 nm. The squared radius of inertia is more preferably from 20 to 200 nm. Also, the cellulose compound (preferably the cellulose acylate) is preferably dissolved such that the second virial coefficient becomes from $-2\times10^{-4}$ to $4\times10^{-4}$. The second virial coefficient is more preferably from $-2\times10^{-4}$ to $2\times10^{-4}$. The definitions of aggregate molecular weight, squared radius of inertia and second virial coefficient as used in the present invention are described below.

These are measured using a static light scattering process according to the following method. For the convenience's sake of apparatus, the measurement is performed in the dilute region, but these measured values reflect the behavior of dope in the high-concentration region. First, solutions of 0.1 mass %, 0.2 mass %, 0.3 mass % or 0.4 mass % are prepared by dissolving cellulose acylate in a solvent which is used for the dope. Here, in order to prevent absorption of moisture, cellulose acylate dried at 120° C. for 2 hours is used and weighed at 25° C. and 10% RH. The dissolution is performed by the method employed at the dissolution of dope (ordinary temperature dissolution, cooling dissolution or high temperature dissolution).

Subsequently, these solutions with solvent are filtered through a 0.2 µm membrane filter (PTFE (Polytetrafluoroethylene)-made), and static light scattering of each filtered solution is measured at 25° C. using a light scattering spectrophotometer DLS-700 (trade name, manufactured by Otsuka Electronics Co., Ltd.) in 10° steps from 30° to 140°. The obtained data are analyzed by the BERRY plotting method. At this time, the value of the solvent determined by Abbe refraction system is used as the refractive index necessary for the analysis, and the concentration gradient (dn/dc) of refractive index is measured by a differential refractometer DRM-1021 (trade name, manufactured by Otsuka Electronics Co., Ltd.) by using the solvent and solution used for the measurement of light scattering.

In the preparation of the dope solution of cellulose compound, the method for dissolving cellulose compound is not particularly limited, and the dissolution may be performed by a room temperature dissolution method, a cooling dissolution method, a high temperature dissolution method or a combination thereof. These dissolution methods are described as the preparation method of a cellulose compound solution, for example, in JP-A-5-163301, JP-A-61-106628, JP-A-58-127737, JP-A-9-95544, JP-A-10-95854, JP-A-10-45950, JP-A-2000-53784, JP-A-11-322946, JP-A-11-322947, JP-A-2-276830, JP-A-2000-273239, JP-A-11-71463, JP-A-04-259511, JP-A-2000-273184, JP-A-11-323017 and JP-A-11-302388. The methods for dissolving cellulose compounds in an organic solvent described in these patent publications can be appropriately applied also in the present invention as long as it is within the scope of the present invention.

In particular, as for the chlorine-free solvent system, the method described in detail in JIII Journal of Technical Disclosure (No. 2001-1745, pp. 22-25, Japan Institute of Invention and Innovation (Mar. 15, 2001)) can be employed. Furthermore, the dope solution of cellulose compound used in the present invention may be subjected to concentration and filtration of the solution, and these are similarly described in detail in JIII Journal of Technical Disclosure (No. 2001-1745, page 25, Japan Institute of Invention and Innovation (Mar. 15, 2001)). In the case of performing the dissolution at a high temperature, the temperature is most often higher than the boiling point of the organic solvent used and in such a case, the dissolution is performed under pressure.

The cellulose composition of the present invention can be prepared by mixing a solution obtained by dissolving the compound represented by Formula (I) or (II) in a suitable solvent with a cellulose compound solution obtained by dissolving the cellulose compound in a suitable solvent. The method of mixing these solutions is not particularly limited, and the solution obtained by mixing the solutions can be used as a dope for preparation of film. In the present invention, the order of adding the cellulose compound and the compound represented by Formula (I) or (II) is not particularly limited, and these solutions may be added simultaneously. The concentration of the cellulose compound in the dope is preferably 10 to 30 mass %, more preferably 13 to 27 mass %, and particularly preferably 15 to 25 mass %. The method of dissolving the cellulose compound is not particularly limited as long as the dope having the above concentration is obtained. The examples of the method include; controlling the concentration in dissolving step of the cellulose compound; preparing a desired high-concentration solution by a concentration step described below after preparing a low-concentration solution (for example, 9 to 14 mass %); and preparing a desired concentration solution by adding various additives after preparing a high-concentration solution.

A solvent for dissolving the compound represented by Formula (I) or (II) can be used the solvent similar to that used for dissolving the cellulose compound described above. The concentration of the compound represented by Formula (I) or (II) in the dope is, for example, 0.1 to 30 mass %, preferably 1 to 15 mass %.

The dope solution containing cellulose compound preferably has a viscosity and a dynamic storage modulus in the following ranges, because the casting is facilitated. A sample solution (1 mL) is measured using "Steel Cone (trade name)" with a diameter of 4 cm/2° in a rheometer "CLS 500 (trade name)" (both manufactured by TA Instruments). The measurement is performed under the prescribed conditions of the apparatus (oscillation step/temperature ramp) by varying the temperature at 2° C./min in the range from 40° C. to −10° C., and the static non-Newton viscosity n*(Pa·s) at 40° C. and the storage modulus G' (Pa) at −5° C. are determined. Incidentally, the measurement is started after previously keeping the sample solution at the measurement initiation temperature until the liquid temperature becomes constant. In the present invention, the dope preferably has a viscosity of 1 to 400 Pa·s at 40° C. and a dynamic storage modulus of 500 Pa or more at 15° C., more preferably a viscosity of 10 to 200 Pa·s at 40° C. and a dynamic storage modulus of 100 to 1,000,000 Pa at 15° C. Furthermore, the dynamic storage modulus at low temperature is preferably larger and, for example, when the casting support is at −5° C., the dynamic storage modulus at −5° C. is preferably from 10,000 to 1,000,000 Pa, and when the support is at −50° C., the dynamic storage modulus at −50° C. is preferably from 10,000 to 5,000,000 Pa.

[Cellulose Film]

The cellulose film of the present invention comprises the cellulose composition of the present invention described above.

Hereinafter, the method of producing the cellulose film of the present invention will be described in detail.

As for the method and apparatus for film formation, the solution casting film formation method and solution casting film formation apparatus conventionally used for the production of cellulose triacetate film are used. Hereinafter, the specific examples will be explained. The dope (cellulose composition solution) prepared in a dissolving machine (kettle) is once stored in a storing kettle and finalized by removing the bubbles contained in the dope. The dope is supplied to a pressure-type die from the dope discharge port through, for example, a pressure-type quantitative gear pump capable of feeding a constant amount of solution with high precision by the number of rotations, and uniformly cast on an endlessly running metal support in the casting part from the mouth ring (slit) of the pressure-type die, and the damp-dry dope film (also called web) is peeled off from the metal support at the peeling point after nearly one round of the metal support.

The obtained web is nipped by clips at both ends, conveyed by a tenter while keeping the width, thereby dried, then conveyed by a roll group of a drying apparatus to complete the drying, and taken up to a predetermined length by a take-up machine. The combination of the tenter and the drying apparatus comprising a roll group varies depending on the purpose. In the solution casting film formation method used for a silver halide photographic light-sensitive material or a functional protective film of electronic displays, in addition to the solution casting film formation apparatus, a coating apparatus is added in many cases so as to apply surface treatment to the film, such as subbing layer, antistatic layer, antihalation layer and protective layer. These respective manufacturing steps are described in detail in JIII Journal of Technical Disclosure (No. 2001-1745, issued Mar. 15, 2001 (pages 25 to 30) by Japan Institute of Invention and Innovation) and are classified into casting (including cocasting), a metal support, drying, stripping (peeling), stretching and the like.

Here, in the invention, though a space temperature of the casting section is not particularly limited, it is preferably from −50 to 50° C., more preferably from −30 to 40° C., and especially preferably from −20 to 30° C. In particular, a dope obtained by casting at a low space temperature is cooled in a moment on the support and increased in gel strength, whereby its organic solvent-containing film can be kept. As a result, it is possible to strip off the film from the support within a short period of time without evaporating the organic solvent from the cellulose compound. Thus, high-speed casting can be achieved. The measure for cooling the space is not particularly limited, and those using usual air or nitrogen, argon, helium or the like are employable. Also, in that case, the relative humidity is preferably from 0 to 70%, and more preferably from 0 to 50%. Also, in the present invention, the temperature of the support in the casting section for casting the dope is from −50 to 130° C., preferably from −30 to 25° C., and more preferably from −20 to 15° C. In order to keep the casting section at the desired temperature, a cooled gas may be introduced into the casting section, or the space may be cooled by disposing a cooling unit in the casting section. At that time, it is important to take care such that water does not attach. Such can be achieved by a method of utilizing a dried gas or the like.

In the present invention, with respect to the contents of each layer and casting, the following configuration is especially preferable. That is, a dope containing at least one plasticizer which is liquid or solid at 25° C. in an amount of from 0.1 to 20% by mass relative to the cellulose compound; a dope containing at least one liquid or solid ultraviolet absorber in an amount of from 0.001 to 5% by mass relative to the cellulose compound; a dope containing at least one solid fine particle powder having an average particle size of from 5 to 3,000 nm in an amount of from 0.001 to 5% by mass relative to the cellulose compound; a dope containing at least one fluorine based surfactant in an amount of from 0.001 to 2% by mass relative to the cellulose compound; a dope containing at least one stripping agent in an amount of 0.0001 to 2% by mass relative to the cellulose compound; a dope containing at least one anti-degradation agent in an amount of from 0.0001 to 2% by mass relative to the cellulose compound; a dope containing at least one optical anisotropy controlling agent in an amount of from 0.1 to 15% by mass relative to the cellulose compound; a dope containing at least one infrared absorber in an amount of from 0.1 to 5% by mass relative to the cellulose compound; and a cellulose film (preferably a cellulose acylate film) prepared therefrom are preferable.

In the casting step, one kind of the dope may be subjected to single-layered casting, or two or more kinds of dopes may be subjected to simultaneous and/or successive cocasting. In the case of including a casting step of two or more layers, the dope and the cellulose film prepared are a dope and a cellulose film (preferably a cellulose acylate film), respectively, each of which is characterized in that the composition of the chlorine based solvent of each of the layers is either the same or different; that the additive of each of the layers is either one kind or a mixture of two or more kinds; that the addition position of the additive in each of the layers is either the same layer or a different layer; that the concentration of the additive in the solution in each of the layers is either the same or different; that the molecular weight of an associate of each of the layers is either the same or different; that the temperature of the solution of each of the layers is either the same or different; that the coating amount of each of the layers is either the same or different; that the viscosity of each of the layers is either the same or different; that the film thickness after drying of each of the layers is either the same or different; that the materials existing in each of the layers are dispersed in either the same state or a different state; that the physical properties of each of the layers are either the same or different; and that the physical properties of each of the layers are of distribution in physical properties either in a uniform state or a varied state, are preferable.

The physical properties as referred to herein include physical properties described in detail in JIII Journal of Technical Disclosure (No. 2001-1745, issued Mar. 15, 2001 (pages 6 to 7) by Japan Institute of Invention and Innovation). Examples thereof include haze, transmittance, spectral characteristics, retardation (Re), retardation (Rth), molecular orientation axis, axis displacement, tear strength, folding strength, tensile strength, difference in Rt of inner and outer windings, creaking, kinetic friction, alkaline hydrolysis, curl value, water content, amount of residual solvent, thermal shrinkage, high-humidity dimensional evaluation, water vapor permeability, planarity of a base, dimensional stability, thermal shrinkage starting temperature, elastic moduhlis and measurement of bright spot foreign matter. Examples thereof further include impedance and surface condition to be used for the evaluation of a base. Also, yellow index, transparency and thermal physical properties (for example, Tg and crystallization heat) as described in detail in JIII Journal of Technical Disclosure (No. 2001-1745, issued Mar. 15, 2001 (page 11) by Japan Institute of Invention and Innovation) can be exemplified.

The cellulose film of the present invention may be stretched. It is particularly preferable that the film is stretched at a given rate for expression of optical anisotropy.

Any known method may be used for stretching and, for example, the cellulose film can be stretched by a uniaxial roll stretching, uniaxial tenter stretching, simultaneous biaxial stretching, consecutive biaxial stretching or inflation process at a temperature in the range of 10° C. to 50° C. higher than its glass transition temperature (Tg). In the case of film production by solution casting method, the film can be stretched at a residual solvent content in the range of 1 to 30%, more preferably in the range of 5 to 20%. The stretch ratio preferably used is 1.1 to 3.5.

The cellulose film may be subjected to a surface treatment as the case may be, thereby achieving an enhancement of adhesion between the cellulose film and each of functional layers (for example, an undercoat layer and a backing layer). For example, a glow discharge treatment, an ultraviolet irradiation treatment, a corona treatment, a flame treatment or an acid or alkali treatment can be employed. The glow discharge treatment as referred to herein may be a treatment with a low-temperature plasma occurring under a low-pressure gas of from $10 \times 10^{-3}$ to 20 Ton (0.133 Pa to 2.67 kPa), and furthermore, a treatment with a plasma under an atmospheric pressure is also preferable.

A plasma excitation gas means a gas which is plasma-excited under the foregoing condition, and examples thereof include argon, helium, neon, krypton, xenon, nitrogen, carbon dioxide, fluorocarbons such as tetrafluoromethane and mixtures thereof. Such is described in detail in Journal of Technical Disclosure (No. 2001-1745, issued Mar. 15, 2001 (pages 30 to 32) by Japan Institute of Invention and Innovation). For the plasma treatment under an atmospheric pressure, which has recently been watched, for example, irradiation energy of from 20 to 500 kGy at from 10 to 1,000 keV is preferably used, and irradiation energy of from 20 to 300 kGy at from 30 to 500 keV is more preferably used. Above of all, an alkali saponification treatment is especially preferable, and this is extremely effective as a surface treatment for the cellulose acylate film.

The alkali saponification treatment may be carried out by coating with a saponification liquid. In the case of the coating method, a dip coating method, a curtain coating method, an extrusion coating method, a bar coating method and an E type coating method can be employed. It is preferable that a solvent having good wettability for coating the saponification liquid on a transparent support and keeping a surface condition good without causing unevenness on the surface of the transparent support by the solvent of the saponification liquid is chosen as a solvent for the alkali saponification treatment coating solution. Specifically, an alcohol based solvent is preferable, and isopropyl alcohol is especially preferable.

Also, an aqueous solution of a surfactant can be used as the solvent. The alkali of the alkali saponification coating solution is preferably an alkali which is soluble in the foregoing solvent, and more preferably KOH or NaOH. The pH of the saponification coating solution is preferably 10 or more, and more preferably 12 or more. With respect to the reaction condition at the time of the alkali saponification, the reaction is preferably carried out at room temperature for from one second to 5 minutes, more preferably from 5 seconds to 5 minutes, and especially preferably from 20 seconds to 3 minutes. After the alkali saponification reaction, it is preferable that the surface coated with the saponification liquid is washed with water or rinsed with an acid and then washed with water. Also, a coating type saponification treatment and provision of an oriented film as described later can be continuously carried out, whereby the number of steps can be reduced.

In bonding the film to the emulsion layer, it is possible to achieve favorable adhesion, by surface-activating the cellulose film and then coating a functional layer directly thereon or by forming an undercoat layer (adhesive layer) previously without or with some surface treatment and coating an additional functional layer thereon. Details of the undercoat layer is described in detail in MI Journal of Technical Disclosure (No. 2001-1745, issued Mar. 15, 2001 (page 32) by Japan Institute of Invention and Innovation). In addition, various functional layers preferable as the functional layers for the cellulose film of the present invention are also described in detail in JIII Journal of Technical Disclosure (No. 2001-1745, issued Mar. 15, 2001 (pages 32 to 45) by Japan Institute of Invention and Innovation).

It is preferable to adjust the kind and/or addition amount of the compound represented by Formula (I) or (II) (retardation-increasing agent) used and/or the film stretch ratio properly, for control of the values Re and Rth of the cellulose film of the present invention respectively in preferable ranges. In particular, it is possible according to the present invention to obtain a cellulose film having desired Re and Rth values, by selecting a retardation-increasing agent giving a desirable Rth value and also determining the addition amount of the retardation-increasing agent and the film stretch ratio properly so that a desired Re value is obtained.

In the present invention, $Re(\lambda)$ and $Rth(\lambda)$ indicate the in-plane retardation and the retardation in a thickness direction, respectively, at a wavelength of $\lambda$. $Re(\lambda)$ is measured by making light at a wavelength of $\lambda$ nm to be incident in the film normal direction in KOBRA 21ADH or WR (trade names, manufactured by Oji Scientific Instruments). The measurement wavelength ($\lambda$ nm) can be selected by manual exchange of wavelength selection filters or the retardation can be calculated from observed values by conversion, for example using a suitable program.

In the case where the film measured is a film expressed by a uniaxial or biaxial refractive index ellipsoid, the Rth(λ) is calculated by the following method. The above-described Re(λ) is measured at 6 points in total by making light at a wavelength of λ nm to be incident from directions inclined with respect to the film normal direction in 10° steps up to 50° on one side from the normal direction with the in-plane slow axis (judged by KOBRA 21ADH or WR) being used as the inclination axis (rotation axis) (when the slow axis is not present, an arbitrary direction in the film plane is used as the rotation axis) and based on the retardation values measured, the assumed value of average refractive index and the film thickness value input, Rth(λ) is calculated by KOBRA 21ADH or WR.

In the above, when the film has a direction where the retardation value becomes zero at a certain inclination angle from the normal direction with the rotation axis being the in-plane slow axis, the retardation value at an inclination angle larger than that inclination angle is calculated by KOBRA 21 ADH or WR after converting its sign into a negative sign.

Incidentally, after measuring the retardation values from two arbitrary inclined directions by using the slow axis as the inclination axis (rotation axis) (when the slow axis is not present, an arbitrary direction in the film plane is used as the rotation axis), based on the values obtained, the assumed value of average refractive index and the film thickness value input, Rth can also be calculated according to the following formulae (1) and (2).

$$Re(\theta) = \left[ nx - \frac{ny \times nz}{\sqrt{\left\{ny \sin\left(\sin^{-1}\left(\frac{\sin(\theta)}{nx}\right)\right)\right\}^2 + \left\{nz \cos\left(\sin^{-1}\left(\frac{\sin(\theta)}{nx}\right)\right)\right\}^2}} \right] \times \frac{d}{\cos\left\{\sin^{-1}\left(\frac{\sin(\theta)}{nx}\right)\right\}}$$ Formula (1)

Note:

In formula (1), Re(θ) represents the retardation value in the direction inclined at an angle of θ from the normal direction, nx represents the refractive index in the in-plane slow axis direction, ny represents the refractive index in the direction crossing with nx at right angles in the plane, nz represents the refractive index in the direction crossing with nx and ny at right angles, and d represents the film thickness.

$$Rth = ((nx+ny)/2 - nz)d$$ formula (2)

In the case where the film measured is a film incapable of being expressed by a uniaxial or biaxial refractive index ellipsoid or a film not having a so-called optic axis, Rth(λ) is calculated by the following method.

The Re(λ) is measured at 11 points by making light at a wavelength of λ nm to be incident from directions inclined with respect the film normal direction in 10° steps from −50° to +50° with the in-plane slow axis (judged by KOBRA 21ADH or WR) being used as the inclination axis (rotation axis) and based on the retardation values measured, the assumed value of average refractive index and the film thickness value input, Rth(λ) is calculated by KOBRA 21ADH or WR.

In the measurement above, as for the assumed value of average refractive index, those described in Polymer Handbook (John Wiley & Sons, Inc.) and catalogues of various optical films can be used. The average refractive index of which value is unknown can be measured by an Abbe refractometer. The values of average refractive index of main optical films are as follows: cellulose acylate (1.48), cycloolefin polymer (1.52), polycarbonate (1.59), polymethyl methacrylate (1.49) and polystyrene (1.59). When such an assumed value of average refractive index and the film thickness are input, KOBRA 21ADH or WR calculates nx, ny and nz and from these calculated nx, ny and nz, Nz=(nx−nz)/(nx−ny) is further calculated.

First, applications of the cellulose film of the present invention will be described below briefly.

The cellulose film of the present invention is useful as optical films, in particular as a polarizing plate protective film, an optical compensation sheet (also called phase difference film) for liquid crystal display devices, an optical compensation sheet for reflective liquid crystal display devices, and a support for silver halide photographic light-sensitive materials.

Thus, the thickness of the film of the present invention varies according to applications, and is not particularly limited, but preferably 30 μm or more, more preferably 30 to 200 μm.

In the case where the cellulose acylate film of the invention is used as a polarizing plate protective film, the polarizing plate is not particularly limited with respect to the preparation method and can be prepared by a general method. There is a method in which the resulting cellulose acylate film having been subjected to an alkali treatment is stuck on both surfaces of a polarizer prepared by dipping and stretching a polyvinyl alcohol film in an iodine solution by using a completely saponified polyvinyl alcohol aqueous solution. Easy-adhesion processing described in JP-A-6-94915 and JP-A-6-118232 may be applied in place of the alkali treatment. Examples of the adhesive which is used for sticking the treatment surface of the protective film and the polarizer include polyvinyl alcohol based adhesives such as polyvinyl alcohol and polyvinyl butyral; and vinyl based latexes such as butyl acrylate. The polarizing plate is configured of a polarizer and protective films for protecting the both surfaces of the polarizer and further configured such that a protective film is stuck on one of the surfaces of the polarizing plate, with a separate film being stuck on the opposite surface thereto. The protective film and the separate film are used for the purpose of protecting the polarizing plate at the shipment of the polarizing plate, the product inspection and so on.

In that case, the protective film is stuck for the purpose of protecting the surface of the polarizing plate and is used on an opposite surface side to the surface onto which the polarizing plate is stuck to a liquid crystal plate. Also, the separate film is used for the purpose of covering the adhesive layer to be stuck to a liquid crystal plate and is used on a side of the surface onto which the polarizing plate is stuck to a liquid crystal plate. In a liquid crystal display, usually, a substrate containing liquid crystals is disposed between two polarizing plates. A polarizing-plate protective film to which the film of the present invention is applied can exhibit excellent display performances, regardless of the site the film is to be disposed. In particular, because a transparent hard coat layer, an antiglare layer, an anti-reflection layer, and the like layers are disposed to a polarizing-plate protective film to be disposed at the outermost surface at the displaying side of a liquid crystal display, employment of the aforementioned polarizing-plate protective film at this site is especially preferable.

The cellulose film of the present invention can be used in various applications, and is particularly effective when used as an optical compensation sheet for liquid crystal display devices. The cellulose film of the present invention can be used in liquid crystal cells having various display modes. As the display mode of the liquid crystal cell, various display modes such as a TN (twisted nematic) mode, an IPS (in-plane switching) mode, an FLC (ferroelectric liquid crystal) mode, an AFLC (anti-ferroelectric liquid crystal) mode, an OCB (optically compensatory bend) mode, an STN (super twisted nematic) mode, a VA (vertically aligned) mode and an HAN (hybrid aligned nematic) mode are proposed. In addition, display modes in combination of the abovementioned display modes different in liquid crystal orientation are also proposed.

The cellulose film of the present invention is also effective, when used in any display mode of liquid crystal display device. Further, the cellulose film of the present invention can be preferably used in any of transparent-type, reflection-type, and semitransparent-type liquid crystal displays. The cellulose film of the present invention can be used as a support for an optical compensation sheet that is used in TN type liquid crystal displays having the liquid crystal cell of TN mode. The cellulose film of the present invention may be also used as a support for an optical compensation sheet that is employed in STN-type liquid crystal displays installing a STN mode liquid crystal cell.

In general, in an STN-mode liquid crystal display device, rod-shaped liquid crystalline molecules in the liquid crystal cell are twisted within a range from 90 to 360 degrees, and the product (And) between the refractive index anisotropy (Δn) of the rod-shaped liquid crystalline molecule and the cell gap (d) falls within a range from 300 to 1500 nm. Optical compensation films used in STN-mode liquid crystal display devices are described in JP-A-2000-105316. The cellulose film according to the embodiment can be used as an optical compensation film or a support of the optical compensation film in a VA-mode liquid crystal display device having a VA (Vertical Alignment)-mode liquid crystal cell. The cellulose film according to the embodiment is also advantageously used as a support of the optical compensation film in an OCB (Optically Compensated Bend)-mode liquid crystal display device having an OCB-mode liquid crystal cell or in a HAN (Hybrid Aligned Nematic)-mode liquid crystal display device having a HAN-mode liquid crystal cell.

The cellulose film can also be advantageously used as an optical compensation sheet for the reflection-type liquid crystal display devices of TN-type, STN-type, HAN-type, or GH (Guest-host)-type. These display modes are well known for a long time. The TN-type reflection-type liquid crystal display devices can be prepared in accordance with, for example, JP-A-10-123478, WO 98/48320, and Japanese Patent No. 3022477. The optical compensation sheet for use in a reflection type liquid crystal display device can be prepared in accordance with, for example, WO 00/65384. The cellulose film of the present invention is also advantageously used as a support of the optical compensation film in an ASM (axially symmetric aligned microcell)-mode liquid crystal display device having an ASM-mode liquid crystal cell. The ASM-mode liquid crystal cell is characterized in that the cell thickness is held by a position-adjustable resin spacer.

Other properties of the liquid crystal cell of ASM mode are similar to the properties of the liquid crystal cell of TN mode. The liquid crystal cells of ASM mode and ASM type liquid crystal display devices can be prepared in accordance with, for example, a paper of Kume et al. (Kume et al., SID 98 Digest, P. 1089 (1998)). The detailed applications of the cellulose film described above are described in JIII Journal of Technical Disclosure (No. 2001-1745, issued Mar. 15, 2001 (pages 45 to 59) by Japan Institute of Invention and Innovation).

According to the present invention it is to provide a novel compound that can be used as a retardation-increasing agent to be able to provide an optical film with desired retardation without causing the problem of bleeding out; and to provide a cellulose film excellent in durability. According to the present invention it is also to provide a liquid crystal display device employing an optically anisotropic transparent support containing the retardation-increasing agent that is superior in image display characteristics (particularly with expanded view angle and with less fluctuation in color).

The glucose compound of the present invention is superior in retardation-increasing efficiency and resistant to precipitation thereof on the surface of the cellulose film, and does not cause the problem of bleeding out. The cellulose film containing the same is superior in optical anisotropy and durability.

The present invention will be described in more detail based on the following examples. Any materials, reagents, amount and ratio of use and operations, as shown in the examples, may appropriately be modified without departing from the spirit and scope of the present invention. It is therefore understood that the present invention is by no means intended to be limited to the specific examples below.

EXAMPLES

Synthesis of the Compounds Represented by Formula (I) and (II)

Example 1

Synthesis of Exemplified Compound A-2 (m=0, n=0)

The exemplified compound A-2 (m=0, n=0) was synthesized, according to the following scheme.

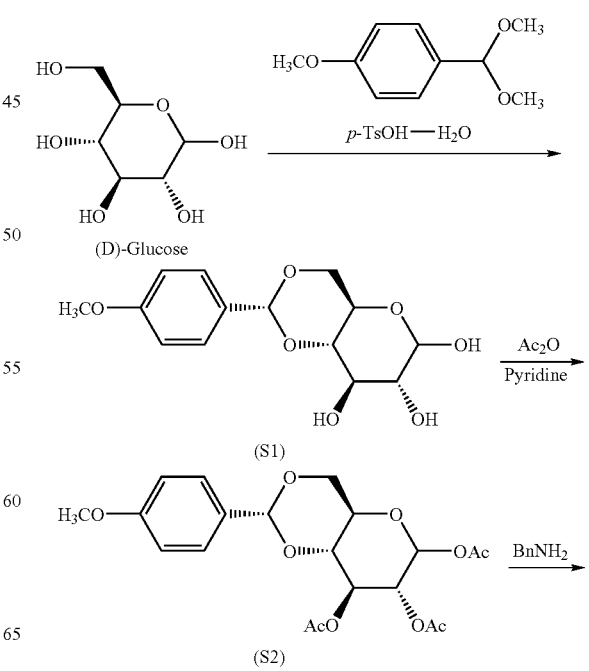

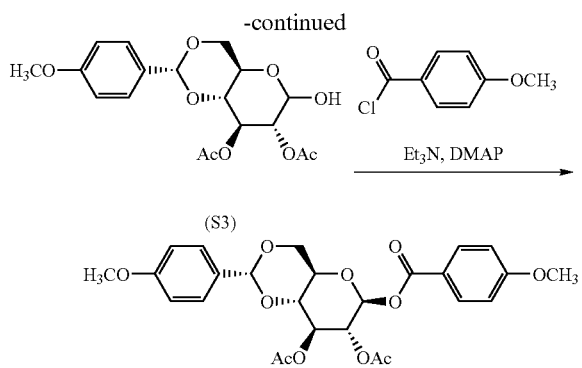

Exemplified compound A-2 (m = 0, n = 0)

[Synthesis of Intermediate S1]

50 g of D-glucose, 52 ml of 4-methoxybenzaldehyde dimethylacetal, and 45 mg of p-toluenesulfonic acid monohydrate were added to 200 ml of dimethylacetamide (DMAc), and the mixture was stirred at 60° C. for 1 hour under reduced pressure (130 mm Hg). Then, 1.5 ml of triethylamine was added to the reaction solution; volatile components were removed; and the residue was purified by silica gel chromatography, to give an intermediate S1 as white solid (41 g).

[Synthesis of Intermediate S2]

50 ml of acetic anhydride was added gradually, dropwise to a suspension of the intermediate S1 (41 g) in 100 ml of pyridine, as the mixture was cooled on ice. After dropwise addition, the mixture was warmed to room temperature and stirred for 12 hours, and then, volatile components were removed under reduced pressure. 100 ml of water was added to the residue; the mixture was extracted with ethyl acetate; and the organic layer was dried over anhydrous magnesium sulfate. After removal of solvent, the residue was recrystallized form ethyl acetate/hexane, to give an intermediate S2 as white solid (53 g).

[Synthesis of Intermediate S3]

The intermediate S2 (13.1 g) and 3.9 ml of benzylamine were added to 250 ml of tetrahydrofuran; the mixture was stirred at 40° C. for 22 hours; 50 ml of 0.25 N hydrochloric acid was added to the reaction solution; and the mixture was extracted with ethyl acetate, and the organic layer was washed with saturated aqueous sodium bicarbonate solution and then dried over anhydrous magnesium sulfate. After removal of solvent, the residue was recrystallized form ethyl acetate/hexane, to give an intermediate S3 as white solid (10.3 g).

[Synthesis of Exemplified Compound A-2 (m=0, n=0)]

3.35 g of 4-methoxybenzoyl chloride was added dropwise to a suspension containing the intermediate S3 (5.0 g), 3.7 ml of triethylamine and 80 mg of dimethylaminopyridine (DMAP) in 100 ml of tetrahydrofuran, and the mixture was stirred at room temperature for 2 hours. After reaction, 100 ml of water was added to the reaction solution and the mixture was extracted with ethyl acetate. The organic layer was washed with saturated aqueous ammonium chloride solution and dried over anhydrous magnesium sulfate. After removal of solvent, the residue was recrystallized form ethyl acetate/hexane, to give an exemplified compound A-2 (m=0, n=0) as white solid (4.51 g).

The compound was identified by $^1$H-NMR.

$^1$H-NMR spectral data (CDCl$_3$): 8.00 (2H, m), 7.38 (2H, m), 6.94 (2H, m), 6.89 (2H, m), 5.97 (1H, d, J=8.0 Hz), 5.48 (1H, s), 5.44 (1H, t, J=9.2 Hz), 5.33 (1H, dd, J=9.2, 8.0 Hz), 4.40 (1H, m), 3.87 (3H, s), 3.80 (3H, s), 3.81-3.75 (3H, m), 2.08 (3H, s), 2.00 (3H, s)

The melting point of the compound obtained was 233° C.

Examples 2 and 3

Synthesis of Exemplified Compound B-2 (m=0, n=0) and Exemplified Compound B-6 (m=0, n=0)

The exemplified compounds B-2 (m=0, n=0) and B-6 (m=0, n=0) were synthesized, according to the following scheme.

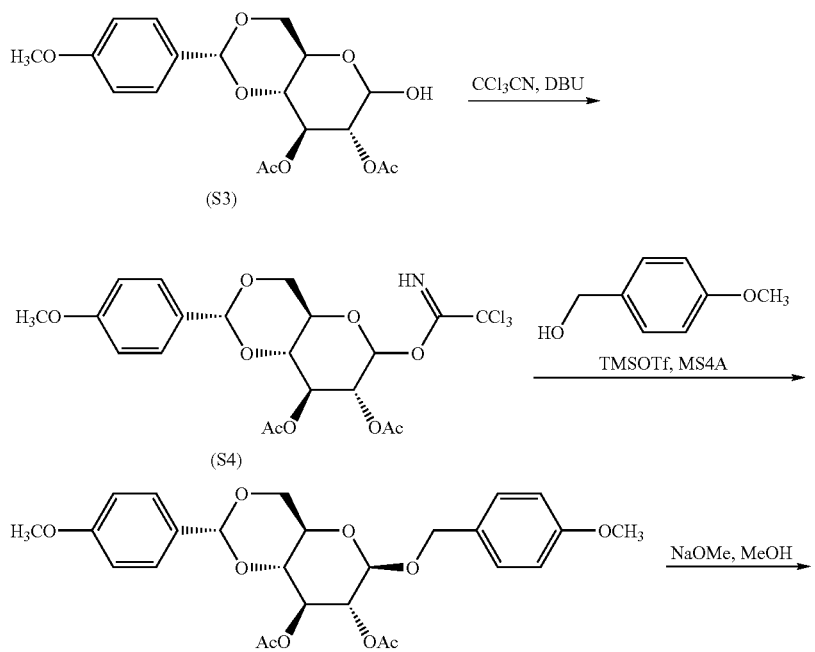

Exemplified compound B-2 (m = 0, n = 0)

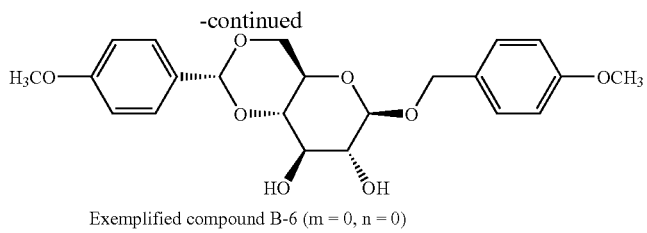

Exemplified compound B-6 (m = 0, n = 0)

[Synthesis of Intermediate S4]

185 µl of 1,8-diazabicyclo[5.4.0]undec-7-ene (DBU) was added to 4.7 g of the intermediate S3 and 2.48 ml of trichloroacetonitrile in 40 ml of dichloromethane, and the mixture was stirred at room temperature for 2 hours. After volatile components were removed, the residue was purified by alumina column chromatography, to give an intermediate S4 as colorless oily matter (3.77 g).

[Synthesis of Exemplified Compound B-2 (m=0, n=0)]

The intermediate S4 (3.77 g), 2.0 g of 4-methoxybenzyl alcohol and 6.0 g of dry molecular sieves 4A (MS 4A) were added to 50 ml of dehydrated dichloromethane, and the mixture was stirred at room temperature for 2 hours. The liquid mixture was cooled to −50° C. while stirred, and 65 µl of trimethylsilyltrifluoromethanoic acid was added dropwise thereto, and the reaction solution was warmed to −20° C. The reaction solution was stirred at the same temperature for 4 hours; saturated aqueous sodium bicarbonate solution was then added to the reaction solution; and the mixture was warmed to room temperature. The liquid mixture was filtered with Celite and extracted with ethyl acetate, and the organic layer was dried over anhydrous magnesium sulfate. After removal of solvent, the residue was recrystallized form ethyl acetate/hexane, to give an exemplified compound B-2 (m=0, n=0) as white solid (2.24 g).

The compound was identified by $^1$H-NMR.

$^1$H-NMR spectral data (CDCl$_3$): 7.35 (2H, m), 7.21 (2H, m), 6.89 (2H, m), 6.86 (2H, m), 5.46 (1H, s), 5.26 (1H, t, J=9.2 Hz), 5.03 (1H, dd, J=9.6, 8.0 Hz), 4.82 (1H, d, J=11.6 Hz), 4.61 (1H, d, J=8.0 Hz), 4.56 (1H, d, J=11.6 Hz), 4.37 (1H, dd, J=10.4, 4.8 Hz), 3.81 (3H, s), 3.80 (1H, dd, J=10.4, 9.6 Hz), 3.79 (3H, s), 3.69 (1H, t, J=9.6 Hz), 3.49 (1H, td, J=9.6, 4.8 Hz), 2.04 (3H, s), 2.01 (3H, s)

The melting point of the compound obtained was 189° C.

[Synthesis of Exemplified Compound B-6 (m=0, n=0)]

400 mg of sodium methoxide was added to a suspension of 1.50 g of the exemplified compound B-2 (m=0, n=0) in methanol, and the mixture was stirred at 40° C. for 20 hours. After reaction, volatile components were removed under reduced pressure; saturated aqueous ammonium chloride solution was then added to; the mixture was extracted with ethyl acetate; and the organic layer was dried over anhydrous magnesium sulfate. After removal of solvent, the residue was recrystallized form ethyl acetate/hexane, to give an exemplified compound B-6 (m=0, n=0) as white solid (1.01 g).

The compound was identified by $^1$H-NMR.

$^1$H-NMR spectral data (CDCl$_3$):7.41(2H,m), 7.29(2H,m), 6.92-6.86(4H,m), 5.50(1H,s), 4.86(1H,d,J=11.2 Hz), 4.57 (1H,d,J=11.2 Hz), 4.47(1H,d,J=8.0 Hz), 4.35(1H,dd,J=10.4, 5.2 Hz), 3.81(3H,s), 3.81(1H,t,J=10.4 Hz), 3.80(3H,s), 3.79 (1H,t,J=9.2 Hz), 3.55(1H,t,J=9.2 Hz), 3.53(1H,dd,J=9.2, 8.0 Hz), 3.44(1H,td,J=9.6, 5.2 Hz), 2.80(1H,brs,—OH), 2.61 (1H,brs,—OH)

The melting point of the compound obtained was 165° C.

Example 4

Preparation of Cellulose Acetate Film

Cellulose Acetate Solution was prepared by charging the following compositions into a mixing tank and stirring it under heating to dissolve respective components.
(Composition of Cellulose Acetate Solution)

| | |
|---|---|
| Cellulose Acetate of acetyl substitution degree of 2.44 | 100.0 parts by mass |
| Methylene chloride (first solvent) | 318 parts by mass |
| Methanol (second solvent) | 47 parts by mass |

16 parts by mass of an exemplified compound A-2 (m=0, n=0), B-2 (m=0, n=0) or B-6 (m=0, n=0) or a comparative compound, 87 parts by mass of methylene chloride and 13 parts by mass of methanol were placed in a separate mixing tank, and the mixture was stirred under heat, to give a retardation-increasing agent solution.

465 parts by mass of the cellulose acetate solution and 36 parts by mass of the retardation-increasing agent solution were mixed, and the mixture was stirred sufficiently, to give a dope. The retardation-increasing agent was added in the amount shown in Table 1 with respect to 100 parts by mass of cellulose acetate.

The dope thus obtained was cast by using a band casting machine. The film at a residual solvent content of 15 mass % was stretched crosswise at a stretch ratio of 30% under a condition of 200° C. in a tenter, to give a cellulose acetate film (thickness: 50 µm).

The Re and Rth retardation values of each cellulose acetate film prepared were measured by using KOBRA (WR, trade name, manufactured by Oji Scientific Instruments Co., Ltd.) at wavelengths of 446 nm, 548 nm and 629 nm were measured in an environment of 25° C. and a relative humidity of 60%.

The durability of the films was evaluated by visual observation of bleeding out after thermo-treatment in an environment of 60° C. and a humidity of 90% for 7 days.

TABLE 1

| Film No. | Additive | Additive amount (parts by mass) | Film thickness (µm) | Re(548) (nm) | Re(629)-Re(446) (nm) | Rth(548) (nm) | Rth(629)-Rth(446) (nm) | Durability* | Remarks |
|---|---|---|---|---|---|---|---|---|---|
| 1 | Compound A-2 (m = 0, n = 0) | 2 | 50 | 46 | 5 | 134 | 11 | ○ | This invention |
| 2 | Compound A-2 (m = 0, n = 0) | 4 | 50 | 57 | 4 | 146 | 9 | ○ | This invention |

TABLE 1-continued

| Film No. | Additive | Additive amount (parts by mass) | Film thickness (μm) | Re(548) (nm) | Re(629)-Re(446) (nm) | Rth(548) (nm) | Rth(629)-Rth(446) (nm) | Durability* | Remarks |
|---|---|---|---|---|---|---|---|---|---|
| 3 | Compound B-2 (m = 0, n = 0) | 2 | 52 | 43 | 5.5 | 123 | 12 | ○ | This invention |
| 4 | Compound B-2 (m = 0, n = 0) | 4 | 50 | 51 | 4.5 | 129 | 10 | ○ | This invention |
| 5 | Compound B-6 (m = 0, n = 0) | 2 | 54 | 46 | 5 | 126 | 11 | ○ | This invention |
| 6 | Comparative compound 1 | 2 | 50 | 47 | 5 | 137 | 11 | x | Comparative example |
| 7 | Comparative compound 2 | 2 | 50 | 56 | 1 | 160 | 0 | ○ | Comparative example |
| 8 | — | — | 50 | 35 | 7.5 | 120 | 13 | — | Comparative example |

*Durability: bleeding out after thermo-treatment in an environment of 60° C. and a humidity of 90% for 7 days
○: bleeding out was not shown
x: bleeding out was shown Comparative compound 1 as described in JP-A-2002-296421

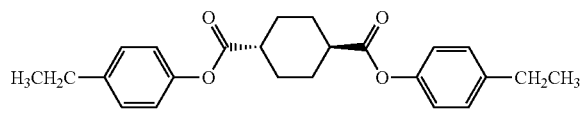

Comparative compound 2 as described in JP-A-2003-344655

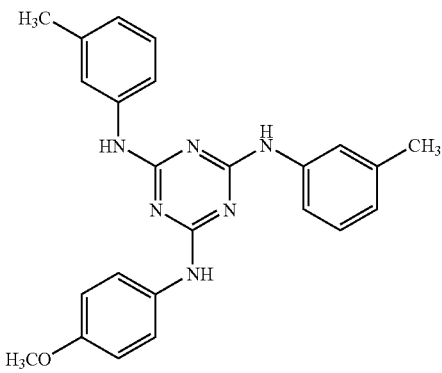

It is apparent from the results shown in Table 1 that the films 1 to 5 containing the compound represented by Formula (I) or (II) of the present invention are higher anisotropic optically than the film 8 containing no compound represented by Formula (I) or (II). It is also apparent that the films 1 to 5 containing the compound represented by Formula (I) or (II) of the present invention did not show bleeding out after thermo-treatment at 60° C. and a humidity of 90% for 7 days, demonstrating their excellent durability. In contrast, the film 6 containing the comparative compound 1 showed the bleeding out. Further, the films 1 to 5 containing the compound represented by Formula (I) or (II) of the present invention favorably retained their reverse dispersibility (Re(629)-Re(446), Rth(629)-Rth(446)). In contrast, the film 7 containing the comparative compound 2 had almost complete loss of reverse dispersibility.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority under 35 U.S.C. §119 (a) on Patent Application No. 2009-087821 filed in Japan on Mar. 31, 2009, which is entirely herein incorporated by reference.

What we claim is:

1. An optical film, which comprises a cellulose composition comprising at least one cellulose compound and at least one glucose compound represented by Formula (II):

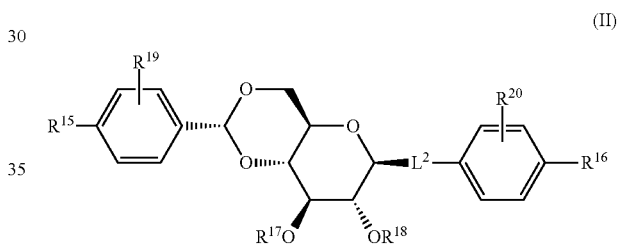

wherein, $R^{15}$ and $R^{16}$ each independently represent an alkyl group having 1 to 6 carbon atoms or an alkenyl group having 2 to 5 carbon atoms, wherein one $CH_2$ group or two or more non-adjacent $CH_2$ groups in the alkyl and alkenyl groups may be replaced by O; $L^2$ represents —OCO—* or —$OCH_2$—*, binding to the phenylene group at the * side; $R^{17}$ and $R^{18}$ each independently represent a hydrogen atom or an acyl group having 1 to 10 carbon atoms; and $R^{19}$ and $R^{20}$ each independently represent a hydrogen atom, a methyl group or a methoxy group.

2. A polarizing plate, comprising a polarization film and two transparent protective films, wherein one transparent protective film is placed on one side of the polarization film and the other transparent protective film is placed on the other side of the polarization film, wherein at least one of the transparent protective films is the optical film according to claim 1.

3. A liquid crystal display device, comprising a liquid crystal cell and two polarizing plates, wherein one polarizing plate is placed on one side of the liquid crystal cell and the other polarizing plate is placed on the other side of the liquid crystal cell, wherein at least one of the polarizing plates is the polarizing plate according to claim 2.

4. The liquid crystal display device according to claim 3, wherein a display mode of the liquid crystal display device is a VA mode.

* * * * *